(12) United States Patent
Kraft

(10) Patent No.: US 10,314,740 B2
(45) Date of Patent: Jun. 11, 2019

(54) EYE DROP DISPENSER

(71) Applicant: Daniel L. Kraft, Stanford, CA (US)

(72) Inventor: Daniel L. Kraft, Stanford, CA (US)

( * ) Notice: Subject to any disclaimer, the term of this patent is extended or adjusted under 35 U.S.C. 154(b) by 448 days.

(21) Appl. No.: 14/345,749

(22) PCT Filed: Sep. 18, 2012

(86) PCT No.: PCT/US2012/055927
§ 371 (c)(1),
(2) Date: Mar. 19, 2014

(87) PCT Pub. No.: WO2013/043607
PCT Pub. Date: Mar. 28, 2013

(65) Prior Publication Data
US 2014/0228783 A1 Aug. 14, 2014

Related U.S. Application Data

(60) Provisional application No. 61/536,053, filed on Sep. 19, 2011.

(51) Int. Cl.
*A61F 9/00* (2006.01)
*G07F 13/06* (2006.01)
(Continued)

(52) U.S. Cl.
CPC .......... *A61F 9/0008* (2013.01); *A61F 9/0026* (2013.01); *G07F 13/06* (2013.01);
(Continued)

(58) Field of Classification Search
CPC ....................................................... A61F 9/00
See application file for complete search history.

(56) References Cited

U.S. PATENT DOCUMENTS

| 4,257,417 A | 3/1981 | Gibilisco | 128/233 |
| 4,685,906 A | 8/1987 | Murphy | 604/300 |

(Continued)

FOREIGN PATENT DOCUMENTS

| JP | H08503164 | 4/1996 | ............... A61F 9/00 |
| JP | 2002034633 | 2/2002 | ............. A45C 13/30 |

(Continued)

OTHER PUBLICATIONS

Communication and Supplementary European Search Report issued in corresponding Application No. 12833135.2-1651, dated Aug. 3, 2015 (10 pgs).

(Continued)

*Primary Examiner* — Tatyana Zalukaeva
*Assistant Examiner* — Sara A Sass
(74) *Attorney, Agent, or Firm* — Hayes Soloway P.C.

(57) ABSTRACT

The present disclosure provides a portable drug dispenser which includes one or more chambers for holding a plurality of separately contained drug products, a dispensing mechanism for accurately dispensing one or more of the plurality of separately contained drugs upon activation of the dispensing mechanism in a specified dose (e.g. specified volume/number of drops) at specified times, and a processor configured to determine the time, and potentially other information such as, e.g. location, patient variables, user data input of each activation of the dispensing mechanism, and an ability to transmit the determined time of activation to a computer located remote to the dispenser, optionally stored on the device as well for read out by a clinician managing the patient.

17 Claims, 2 Drawing Sheets

(51) Int. Cl.
*G07F 15/04* (2006.01)
*G07F 17/00* (2006.01)
*G06F 19/00* (2018.01)
*A61J 1/06* (2006.01)
*A61J 1/20* (2006.01)

(52) U.S. Cl.
CPC .......... *G07F 15/04* (2013.01); *G07F 17/0092* (2013.01); *A61J 1/067* (2013.01); *A61J 1/2093* (2013.01); *G06F 19/3462* (2013.01)

(56) References Cited

U.S. PATENT DOCUMENTS

| | | | | |
|---|---|---|---|---|
| 5,007,905 | A | | 4/1991 | Bauer .......................... 604/295 |
| 5,320,845 | A | * | 6/1994 | Py ........................ A61F 9/0008 424/427 |
| 5,875,931 | A | | 3/1999 | Py ........................ A61M 35/00 |
| 5,893,515 | A | | 4/1999 | Hahn et al. ............... B05B 3/08 |
| 6,355,024 | B1 | * | 3/2002 | Small ...................... A61J 3/002 604/500 |
| 6,450,994 | B1 | * | 9/2002 | Boyles ................. A61F 9/0008 222/420 |
| 2002/0049374 | A1 | | 4/2002 | Abreu .......................... 600/405 |
| 2002/0161344 | A1 | | 10/2002 | Peclat et al. .................. 604/295 |
| 2004/0256487 | A1 | | 12/2004 | Collins, Jr. et al. .......... 239/338 |
| 2005/0001981 | A1 | * | 1/2005 | Anderson ............. A61B 3/113 351/209 |
| 2005/0043692 | A1 | | 2/2005 | Ling ............................ 604/289 |
| 2007/0186923 | A1 | * | 8/2007 | Poutiatine ............. A61J 7/0038 128/200.14 |
| 2008/0233053 | A1 | | 9/2008 | Gross et al. .................... 424/45 |
| 2010/0059608 | A1 | | 3/2010 | Obata .......................... 239/690 |
| 2012/0041778 | A1 | * | 2/2012 | Kraft .................. B65D 51/2828 705/2 |

FOREIGN PATENT DOCUMENTS

| | | | |
|---|---|---|---|
| JP | 2007534384 | 11/2007 | ............ A01N 63/00 |
| JP | 2011507631 | 3/2011 | ............ A61F 9/007 |
| WO | WO 00/00242 | 1/2000 | |
| WO | WO2008132848 | 11/2008 | ............ A45D 44/22 |
| WO | WO2011049911 | 4/2011 | ............ A61B 3/113 |

OTHER PUBLICATIONS

Japanese Office Action issued in application No. 2014-530948, dated Jun. 15, 2016 (6 pgs).
European Office Action issued in application No. 12 833 135.2, dated Jun. 24, 2016 (4 pgs).
Communication and Supplementary Partial European Search Report issued in corresponding Application No. 12833135.2-1651/2758014 PCT/US2012055927, dated Apr. 15, 2015 (7 pgs).
International Preliminary Report on Patentability issued in corresponding application No. PCT/US2012/055927, dated Apr. 3, 2014 (7 pgs).
International Search Report issued in corresponding application No. PCT/US2012/055927, dated Nov. 20, 2012 (2 pgs).
Chau, H., "Easy Eye Drops Make Sure You Don't Blink," Jul. 29, 2012, downloaded from http://technabob.com/blog/2012/07/29/easy-eye-drops/ (3pgs).
Japanese Office Action issued in application No. 2014-530948, dated Feb. 2, 2017 (6 pgs).

* cited by examiner

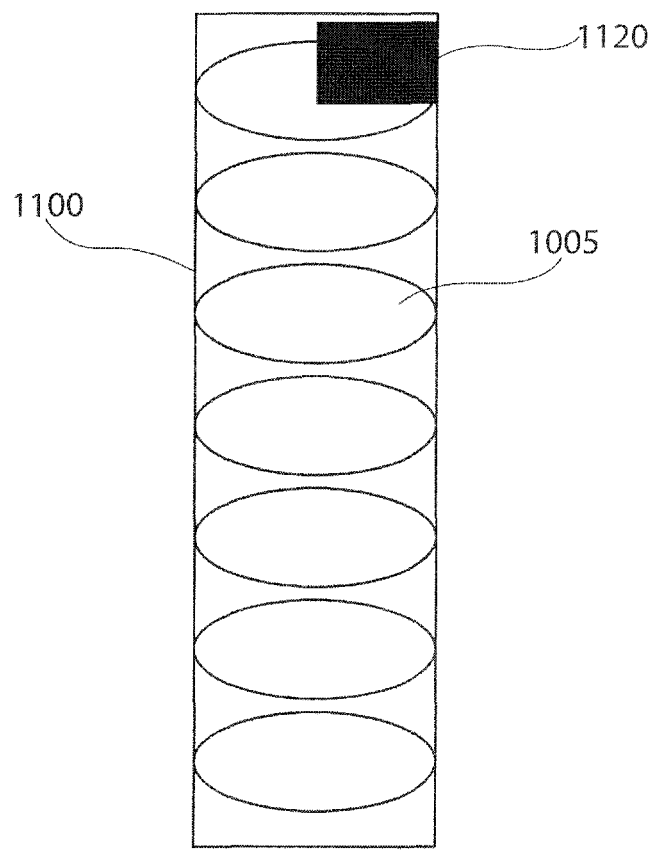
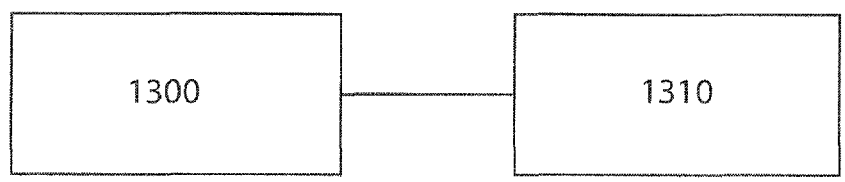
Fig. 3

EYE DROP DISPENSER

CROSS REFERENCE TO RELATED APPLICATION

This Application claims priority from U.S. Provisional Application Ser. No. 61/536,053, filed Sep. 19, 2011, the contents of which are incorporated herein in their entirety by reference.

BACKGROUND OF THE INVENTION

Modern medicine is highly dependent upon medications to prevent, treat and ameliorate diseases and symptoms, including those of the eye. Such medications range from nutrients and vitamins, and other supplements, to prophylactic over-the-counter medications (such as antihistamines and lubricants) to medications for the treatment of diseases (such as glaucoma, retinopathies, uveitis, infections and corneal abrasions).

Many patients with diseases of the eye, and conjunctivae require applications of eye drops (often of different drugs from different dispensers/bottles) one or more times per day.

These eye drops can consist of antibiotics, steroids, prostoglandins, beta-blockers, alpha-andranergic agonists, Carbonic anhydrase inhibitors, Parasympathomimetics, Epinephrine, Hyperosmotic agents, antihistamines, various neuroprotective agents, anti-inflammatory agents, anti-angiogenesis agents, nano-particles, saline, vitamins, lubrication and many others components including existing drops which are already contain various combined medications.

Many patients under the care of an optometrist, opthalmologist or other clinician, take one or more opthalmic medications each day, and in some cases these treatments vary by each eye (i.e. different medications, dosing and timing required for each eye).

Poor compliance/adherence with ophthalmic drop prescriptions is a significant problem and is an increased challenge with the higher number and frequency of different eye drops prescribed. Poor compliance leads to many downsides, including increased disease burden and morbidity, need for surgical interventions (e.g., for glaucoma) and significant overall costs in care. Poor compliance often results in more rapid and/or progressive disease, deteriorated vision, and the need for expensive interventions including eye surgeries.

Compliance to prescribed medication regimens (often termed 'adherence') is often quite low, for example, as low as 50% or lower in many cases. Poor adherence is often exacerbated by complicated instructions, opthalmic drug dispensers (usually simple squeeze bottles) which are difficult to hold and dispense accurately, especially by the elderly. Poor vision, or visual limitations already present may also hamper the ability of the patient or a caregiver to identify visually and select the eye medication of interest, amongst several similar sized or appearing dispensing bottles.

Furthermore, especially in more frail or elderly patients, and those with any tremor or, other movement disorder, or forms of arthritis in the hand, the handling of relatively small eye drop containers can be challenging. The ability to appropriately place the eye drop container over the indicated (eye) and squeeze out an appropriate dose of liquid and having it appropriately administered as directed on the eye, is difficult, including the timing of the eye drop with an open eye, in order to assure the desired medication is delivered.

In addition, clinical trials, and the safety, efficacy measures required to develop new opthalmologic drugs and combinations often require extensive, rigorous and expensive and phased clinical trials. Assurance that trial subjects are actually taking the test drugs/placebo or other medical components is critical to accurate assessment and the potential success of the trials. Better means of tracking compliance during clinical trials will lead to safer, more effective ophthalmologic drugs entering the market.

Another issue of medication dispensation to the eye is the handling and measuring appropriate doses of liquid eye drop medications and delivering properly to the eye. This leads to inaccuracies and the likelihood of missed, under or over dosing.

Accurate dosing and tapering is particularly critical for more potent medications such as steroids and immunosuppressants (such as cyclosprin). Most of these drugs for patients with eye conditions are given outside of the hospital or clinic setting by the patient themselves, family members or other caregivers.

A better, more convenient, integrated method is needed for accurately delivering drugs to the eye, especially for drugs which must be dosed carefully and delivered accurately and regularly.

SUMMARY OF THE INVENTION

The present disclosure is directed, in part, to devices that overcome the aforesaid and other disadvantages of the prior art. Briefly described, the present disclosure provides a portable ophthalmologic drug dispenser that can hold one or a plurality of drug products.

In one aspect, the present disclosure provides a portable drug dispenser which includes one or more chambers for holding a plurality of separately contained drug products, a dispensing mechanism for accurately dispensing one or more of the plurality of separately contained drugs upon activation of the dispensing mechanism in a specified dose (e.g. specified volume/number of drops) at specified times, and a processor configured to determine the time, and potentially other information such as, e.g. location, patient variables, user data input of each activation of the dispensing mechanism, and an ability to transmit the determined time of activation to a computer located remote to the dispenser, optionally stored on the device as well for read out by a clinician managing the patient.

The disclosure enables multiple ophthalmic 'eye' drops to be delivered in a coordinated, tracked, convenient manner and has particular utility for determining, monitoring, and/or ensuring patient compliance as well as the ability to help modulate and adjust medication timing and dosages, and will be described in connection with such utility, although other utilities are contemplated.

The ophthalmologic dispenser could also incorporate various sensors which can measure and/or monitor the patient in any number of ways, including but not limited to measurement of various eye features (e.g. using a light/camera source). Additional sensors such as accelerometers and/or GPS to track movement/location of the individual carrying the dispensing device and location at time of use as well as the orientation of the dispenser can be included to help track location and timing of ophthalmic medicine dispensation. Other measurements of various attributes and communication to the prescribing clinician, or integration with predetermined or other means of varying dosage, timing and other attributes, also can be employed.

In another aspect, the present disclosure provides a portable drug dispenser which includes a first chamber for holding a plurality of a first type of separately contained drug products, one or more additional chambers for holding a plurality of one or more other types of separately contained drug products, respectively, and a dispensing mechanism for dispensing to one or both of the user/patient's eyes one or more of the plurality of separately contained drugs upon activation of the dispensing mechanism.

The disclosure also provides a system, i.e., method and device, for dispensing one or more eye medicines to an individual which can integrate features which include one or more of elements including programmable reminders and scheduling, compliance reminders, compliance tracking and measurement, exact dosing, biomechanical dispensement of fluid drops, feedback mechanisms to enhance compliance and actual delivery of drug/drop to the open eye, and optional features including an ability to communicate wirelessly with one or two way communication to remote computers and databases.

In one embodiment the dispenser contains one or more, for example four different ophthalmic drops (medications) (containing only drugs or other components) which are in liquid form. In such embodiment the medications may be loaded separately into one or more compartments. The medications may be integrated by individual containers or cartridges, for example screwing in the original containers (those in which the medications are regularly dispensed) or in those specially designed to integrate with the dispenser.

In another embodiment, the integrated bottle or similar 'cartridge' containing each medication may include embedded instructions, for example by barcode, via RFID, QR code or other mechanism with which to inform in a hands free manner which medication/cartridge or other form is attached/plugged in/docked with the dispenser.

In yet another embodiment, an entire array of eye medications can be dispensed in proprietary containers, each of which can contain any number of medications to be dispensed. The containers themselves can communicate their contents to the dispenser via RFID, embedded code read by the dispenser, bar code, or any number of mechanisms, including mechanical, shape of aspects of the cartridge, etc.

In a further embodiment the dispenser can be programmed, e.g. by a clinician, pharmacist, patient, caregiver or by instructions indicated from individual containers attached to the dispenser directly via any number of control mechanism for example touch screen, or keypad or via mobile smartphone, via direct port, bluetooth, WiFi, local area network or other wireless mechanism.

In another embodiment the dispenser may include a variety of mechanisms to indicate to the patient/caregiver that prescribed eye drops are due to be dispensed, and optionally other information, e.g. a need for refills, information about each medication, etc. For example, the dispenser may include by visual signals, (such as flashing, glowing or other visual signal, or vibration/'buzzing' similar to a cell phone vibration to indicate a call/message, e.g., by sound, alarm, voice recording, which can be standard/provided or custom recording for example: "Mary, its Dr. Smith . . . it's time to take your eye drops" . . . . Right eye, 2 drops now . . . this will be your morning glaucoma medicine . . . ". Also, instructions can be provided on an integrated screen, which may be a 'touch screen', or by voice which may be computer generated or recorded, for example which could speak instructions such as "Mrs. Jones . . . . Time for drops for your 'RIGHT EYE', two drops . . . . Place dispenser in position and press the dispense button' . . . ". By way of example, the Patient would hold dispenser in position over the appropriate eye, press the dispensing button and appropriate meds (as programmed previously) would be dispensed, either in single or combined drops.

In yet another embodiment a camera is included in the dispenser to record the dispensation, and optionally be utilized to help calculate/optimize timing from drop dispensation and also to record compliance. In a preferred embodiment, the camera or other sensor(s) observes the eye, and when the eye is open, triggers the liquid eye drop to be dispensed, resulting in optimal timing to 'hit' the eye.

In another embodiment the dispensed drops fall via gravity or are forcibly pushed, sprayed or otherwise dispensed into the eye by mechanical mechanism. Each drop, which could vary by each medication/drug dispensed could be programmed or 'tuned' to a very specific volume, i.e. from 10 ul to 200 ul or any other desired volume (consistent with one or more drops. The amount of each dispensation could be programmed into the device by various means, including remotely.)

In another embodiment, a fixed or a flexible patient and/or clinician adjustable bracing mechanism, such as described in U.S. Pat. Nos. 4,257,417, 4,685,906 and 5,007,905, or US Published Application US2005/0043692A1, which are given as non-limiting examples, may be provided to stabilize the dispenser in optimal position over the eye, for example, stabilized by contact with the bridge of the patients nose. This together with/or without the built in camera and/or sensors contained within or on the dispenser this could be utilized to optimally time the release of the drops into the eye, could detect when the eyelids were open, and the dropper in correct relative position over the eye. Also, if desired, a mechanism that helps hold the patient's eyelids open, as described at http://technabob.com/blog/2012/07/29/easy-eye-drops/ may be incorporated into the dispenser.

In still yet another embodiment, drops can be dispensed from any of the, for example, one or more medication containers either singly, i.e. first drop comes from one medication container, and second drop comes from a second medication container. Each medication may be dispensed via the same path. Alternatively, to keep drop lines clear so that the medications are not mixed, each medication may come down a different path. The individual paths could be integrated in with the medication cartridge or container. This enables a completely sterile, 'closed' system by which to assure and enhance sterility, as well as separation of different medications so they would not cross contaminate or mix in the final dispensation path.

In one embodiment a 'Cleaning fluid', e.g. water, saline or other fluid, is utilized to clear, or sterlize the dispensing path to prevent blockage, or between dispensations of individual medications, or following a set or series of dispensations. An integrated and removable cap could be included to keep the dispensing area clean and sterile when the device is not in use.

In one embodiment a battery is included which may be replaceable or rechargeable. In the case of a rechargeable battery the dispenser optionally can be 'docked' with a 'charging station' to maintain a charged battery. Optionally, the medication cartridges themselves may contain a power source.

In another embodiment the medication cartridges contain their own individual fluid path build into each cartridge, to maintain sterility. Also, each cartridge could be queried to check for sterility . . . such queries could include a optical sensor which would measure any degree of cloudiness, suggesting bacterial overgrowth, or changes in conductance or other physical properties. Moreover, the cartridges could report level of fullness, and report a need to order refills, or autonomously trigger thru the internet or other means the ordering of refills, or messages to the ophthalmologist or other prescriber to approve or order medication or other drops for the patient.

In one embodiment the dispenser includes an onboard computer to manage programming, communication in wireless or an option to 'dock' or 'plug in; by various means to separate computer, and database, e.g. electronic medical record or other databases. In such embodiment an optional onboard screen may be provided to communicate visually with instructions, and programmable features. The touch screen option, may include an option to be controlled or programmed by a mobile phone, standard computer or tablet like device or any similar means of electronic data interface.

In another and preferred embodiment, dispenser use can be recorded, and uploaded to the 'cloud', electronic medical record (EMR), Personal health record (PHR) or other database by any number of mechanisms, ranging from direct electric.

In various embodiments the dispenser includes one or more of the following features:
1. A compartment, which can be opened by user, e.g. a sealed door or other mechanism and optionally lined with medical grade plastic or other standard inert lining in which to store ophthalmic solutions;
2. An ability to plug or screw in existing ophthalmic solutions directly into the dispenser;
3. An integrated designed 'cartridges' made to custom fit into one or more slots of the dispenser; and
4. A time stamp recording usage, optional GPS/location determination and other means to record and specify, for recording and optionally transmitting information on usage, compliance over time. This could be queried by patient, caregiver, clinician, nurse or others with appropriate permissions. Data could be designed to be transmitted in a secure, private manner by various standard practices and means.

Further features, functions, and advantages that have been discussed can be achieved independently in various embodiments of the present disclosure or may be combined in yet other embodiments, further details of which can be seen with reference to the following description and drawings, wherein like numerals depict like elements, and wherein:

BRIEF DESCRIPTION OF THE DRAWINGS

FIG. 2 is a view, similar to FIG. 1 of a medication cartridge in accordance with the present disclosure; and FIG. 3 is a flow diagram illustrating tracking use or compliance.

DETAILED DESCRIPTION OF THE INVENTION

Figure 1:
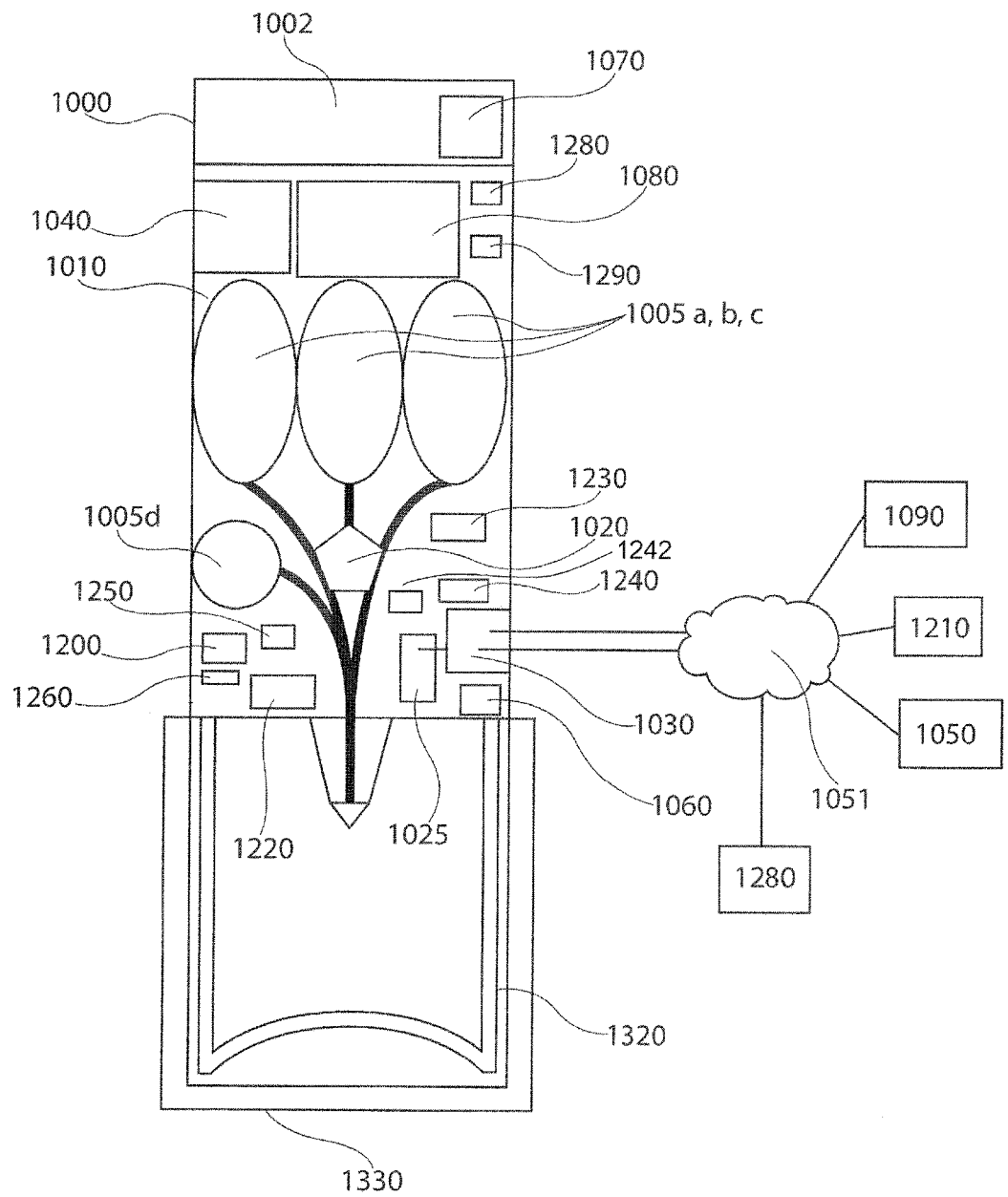
FIG. 1 is a diagrammatic view of an eyedrop dispenser in accordance with the present disclosure.

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

Many embodiments of the invention may take the form of computer-executable instructions, including algorithms executed by a programmable computer (contained within or remote (e.g. via cloud based algorithms and computers). Those skilled in the relevant art will appreciate that the invention can be practiced with other computer system configurations as well. Certain aspects of the disclosure can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices, palmtop computers, implanted and wearable computers, cellular or mobile phones, multi-processor systems, processor-based or programmable consumer electronics, network computers, minicomputers and the like.

The disclosure also can be practiced in distributed computing environments, where tasks or modules are performed by remote processing devices that are linked through a communications network. Moreover, the disclosure can be practiced in Internet-based or cloud computing environments, where shared resources, software and information may be provided to computers and other devices on demand. In a distributed computing environment, program modules or subroutines may be located in both local and remote memory storage devices. Aspects of the disclosure described herein may be stored or distributed on computer-readable media, including magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks. Data structures and transmissions of data particular to aspects of the invention are also encompassed within the scope of the invention. Communication between devices or components provided herein may be accomplished over any wired or wireless network that enables communication between devices, including local area networks (LAN), wide area networks (WAN), the Internet, Wireless LAN, Wi-Fi, mobile device networks, IEEE 802.11, GSM, GPRS, UMTS, WMAN, BWA (LMDS, WiMAX, AIDAAS and HiperMAN), 3G and 4G communications protocols, Bluetooth, or any other network arrangement and/or protocol known to those having ordinary skill in the relevant art. Various standard to advanced means of secure/privacy aspects of data transmission and privacy can be integrated.

The term "drug" or "medication", as used throughout this disclosure, includes pharmaceutical medicines, nutriceuticals, supplements, vitamins, minerals and the like, in any form including drugs commonly used to treat ophthalmologic disorders.

Also, the term "patient" may include both a human patient, and a non-human animal patient. As shown in FIG. 1, a portable drug dispenser 1000 includes a chamber 1010 for holding a plurality of separately contained drug products 1005a, b, c . . . and a wash solution 1005d for cleaning the droplines leading from the plurality of separately contained drug products 1005a, b, c. The separately contained drug products 1005a, b, c . . . may be a combination or compounded drug product, or may be any other drug product. The drug products 1005a, b, c . . . may be in liquid or gel form appropriate for application to the eye. The separately contained drug products 1005a, b, c . . . may include contained quantities of drugs may contain any drug, including nutriceuticals (for example multivitamins), over-the counter-drugs (for example lubricant or anti-redness combination products) and prescription drugs (antibiotics, steroids, prostaglandins, beta-blockers, alpha-andranergic agonists, various hypotensive agents, carbonic anhydrase inhibitors, parasympathomimetics, epinephrine, hyperosmotic agents, various neuroprotective agents, anti-inflammatory agents, anti-angiogenesis agents, nano-particles, saline, vitamins, lubrication and many others components including existing drops which are already contain various combined medications).

The drug products 1005a, b, c . . . may be loaded directly into the chamber 1010. Alternatively, the drug products 1005a, b, c . . . may be loaded into a cartridge 1100 (see FIG. 2) which can be inserted or screwed into the chamber 1010.

The dispenser 1000 includes a dispensing mechanism 1020 for dispensing one or more of the drug products 1005a, b, c . . . . The dispensing mechanism 1020 may include, for example, a microfluidic pump mechanism to dispense a desired volume (i.e. 1 drop, or 0.2 millimeters). When a user pushes the dispensing button, the fluidics are activated and the dispenser 1000 dispenses a single drug from one of the containers. Additional drugs 1005a, b, c . . . may be delivered by subsequent activations. In another embodiment, the dispensing mechanism 1020 may include a battery powered motor which may be activated by operating a switch or button on the dispenser 1000. The battery 1025 may be replaced manually, or recharged by docking the dispenser 1000 or via power cord or other common means of recharging portable devices (e.g., cell phone, via a cord to USB type cable or others.)

The dispenser 1000 may further include a processor 1030, which may be a programmable processor.

One or more drug products 1005a, b, c . . . can be loaded into the ophthalmic dispenser 1000. For example, the dispenser 1000 may be loaded with an antibiotic, or a beta blocker suspension, or alpha-antagonist. These drugs 1005a, b, c . . . could be loaded into the chamber 1010 of the dispenser 1000, into a cartridge 1100 which can be inserted into the chamber 1010 (and which optionally may be removable from the chamber), or other form of holding container in an ordered manner if desired. The end user (e.g., patient or care giver) may place single or multiple (two or more) types of drug products 1005a, b, c . . . into the device. In another embodiment the drugs 1005a, b, c . . . could be provided in a preloaded cartridge. If desired, a drug containing cartridge may include a battery so that a fresh battery is installed in the dispenser each time a fresh cartridge is installed.

By way of example, an individual may be prescribed different medications and doses for the left and right eye: for example 2 drops of Drug A to the right eye (OD) only, 3 times a day and 2 drops of Drug B in Left and Right Eye (OS) once a day. The dispenser could remind the patient or caregiver by various means (such as sound, mechanical buzz, voice notifications, text message) that a eye drop/drug dispensing was indicated at the prescribed times, and the user would then place the dispenser over the appropriate time and the prescribed drug (Drug A and B for the right eye) and drug B only for the right eye. The dispenser could optionally detect by various means (i.e. camera or other sensors, including those to detect upright positioning/orientation in space of the dispenser) whether the dispenser was over the correct eye prior to dispensing the drug in drop form.

In one example, ophthalmic medication is loaded into the device in advance. This could be done by a pharmacist, the patient, a caregiver, or be prescribed as a preloaded cartridge. Each cartridge 1100 can be optionally labeled with machine-readable indicia 1120, which may include patient identification, and/or QR or 'bar-code' of various means. Cartridge 1100 may also contain an RFID type element which can be electronically detected.

The dispenser 1000 may further include a scanning element or reader 1040 for 'reading' the machine-readable indicia 1120 on the cartridge. The reader 1040 may communicate with the processor 1030, and through an internal database, or sourced via internet/cloud based database, the processor 1030 may identify the components of the cartridge, including but not limited to indications and instructions for use of each of the one or more drugs, their dose, expiration date, etc. Controlled release could be moderated manually, by programmed computer, at the designation based on the patient's vital signs or other measurements (i.e. visual acuity, opthalmic pain level, and others).

Each drug product 1005a, b, c . . . dispensed may be recorded, and stored as a record electronically within the dispenser 1000 or transmitted to a remote computer 1050. The dispenser 1000 may transmit information regarding the dispensing of a drug 1005a, b, c . . . over a wireless network 1051, or through a wired network, for example, after 'docking' or plugging in of the device to a computer or network (i.e. to a computer via the USB plug). Each time a drug product 1005a, b, c . . . is dispensed, the processor 1030 may record the time and location of the dispensing. That is, the processor 1030 may provide a time stamp and location information upon activation of the dispensing mechanism 1020. The dispenser 1000 may include a GPS receiver 1200, or utilize any other known system of location tracking, to determine the location of the dispenser when a drug 1005a, b, c . . . is dispensed.

The device may issue an alert, or otherwise indicate to the user/patient when they are due to apply one or more drugs 1005a, b, c . . . to one or both eyes. For example, the dispenser 1000 may include an alert indicator 1070, which may be an audible, visual or physical indicator. For example, the indicator may include a speaker, one or more lights, or a vibrating element. The indicator 1070 may provide the alert by providing an audible sound (e.g., chime, ring, alarm or any other sort of electronic or analog generated sound). The device may issue an alert via a land-line phone or cellular phone call to the user/patient, also via SMS/Text message, or various means of 'push' alerts via any number of mobile or other applications 1210. The device can communicate with one's family or healthcare provider to document proper adherence to a prescribed ophthalmic medical regimen, as well as prevent direct dispensing to unintended recipients.

The dispenser 1000 optionally may include an integrated screen or display 1080 with which to display patient's variables/vitals, or to integrate and display multiple measurements from the patient, environment or other sources. The display 1080 may be a 'touch' screen, with multiple touch controls, and may further provide the user with the ability to load in various applications ('Apps') as appropriate to the desires and needs of the optician, opthalmologist, patient and/or caregiver.

Controls can include but are not limited to 'dispense' controls, to 'refill' buttons which will automatically re-order or request refill from pharmacy and/or physician. These controls may be manually operated, or they may be controlled by the processor 1030.

The data obtained b the dispenser 1000 can flow back to the clinician (for example, by providing the data to a computer 1050 to which the clinician may access) who prescribed the drugs as well as to the patient, family, or assigned caregivers and clinicians. A web or otherwise enabled dashboard (including with appropriate security and privacy measures as are state of the art) can display compliance and timings of dosings from the dispenser 1000 over various time windows. A "dashboard" with various information, including use history, tracking of symptoms, or other information and data can optionally be displayed on the dispenser.

Data and information optionally can be 'pushed' back by the clinician or other caregiver via the device to optimize, change or cancel various prescriptions. For example, a clinician receiving data indicating a patient's glaucoma measurements notes that the pressures have fallen to normal ranges, could indicate via the device/communication to decrease dosing/dispensing. In another example, a clinician managing a patient's eye infection, could receive information from the patient on pain levels, visual acuity, and/or eye exam (communicated via the camera 1220 on the dispenser or other mechanisms including patient entry or data) and alter the timing and dosage of antibioitics.

Tracking of adherence/compliance could be leveraged by 'gamification', such as giving points/badges or other feedback to the individual and optionally integrated with social networks such as FaceBook, or integrated into social gaming, such as those made by Zynga and others. The device could communicate with a mobile phone, for example, to only enable use of 'bonus' features, such as Facebook, or various game type applications, if appropriate medications were taken via the dispenser.

Integration of optional components which measure individual patient metrics could also be integrated into the ophthalmic dispenser. By way of a not limiting example, an accelerometer 1230, which would enable the device to detect positioning of the dispenser, e.g. upright, at an angle, etc., and/or also function as a digital and connected pedometer could be integrated into the dispenser. The dispenser could contain sensors 1240 for measuring biophysical measures of the eye, for example an integrated camera could record and enable analysis of papillary dilation, intraocular pressures, conjunctival redness, or other measures. The camera also could sense an open eye condition, and activate a trigger 1242 to coordinate delivery of a drug product from the dispenser. Additional possible integration sensors could include a glucometer, and other measures of blood biomarkers.

An integrated, connected, or removable cap 1330 could be placed over the dispensing area to keep it clean, and relatively sterile. Placement or positioning of the cap could be measured and stored as part of usage data.

Improved compliance and responsibility for one's own health leads to better outcomes for chronic eye disease and prevention. Employer incentive programs are common, and could leverage the dispenser 1000 to track and encourage compliance to prophylactic (i.e. eye medications for glaucoma) and acute to chronic to disease medications. For example, patient compliance data from the dispenser 1000 (such as the time and location of dispensing) can be transmitted from the dispenser 1000 to a computer 1050 accessible to the patient's insurance provider or employer so that the insurance provider or employer can verify the patient's compliance in taking his/her prescribed medications.

Incentives could be, but are not limited to monetary awards, reductions in insurance premiums, or any number of various rewards, prizes or benefits.

The dispenser 1000 may communicate with any computer 1050, which may include any mobile device such as iPhone, Android or other mobile phone/iPod touches and similar via Bluetooth, direct connection (line) or other standard method of device/device or device to network communication. Information can be transmitted both ways, for example: content from the dispenser 1000 may include reports of times of taking eye medications, number, time stamps, and location (e.g., from GPS integration on the phone or the dispenser 1000). Data can be uploaded via the phone or directly via WiFi, cellular networks or other standard data streams of common use, in secure or unsecure manner to upload information to the dispenser 1000, to include new safety warnings, reminders, updates, schedule changes from the care provider, prescriber or software and feedback algorithms embedded in software based in the cloud, in the patient's and or owners' dispenser 1000, or via their mobile device. The dispenser also could be integrated into and/or attached to a mobile phone case.

The dispenser 1000 optionally may contain two or more types of ophthalmologic drug products 1005$a, b, c$ . . . . For example the primary drop can be a daily steroid (such as dexamethasone), antibiotic (such as Tobramycin), or other medication taken on a regularly scheduled basis, i.e. for glaucoma, post eye surgery, or for prophylactic or other treatment reasons. Should a 'PRN' as needed dose of anti-allergy drops, be needed, a second repository of PRN drugs could be accessed to dispense.

In one iteration, programmable instructions, apps or otherwise integrated into the dispenser could help guide and track a patient through a particular treatment, whether for post-operative care (to include instructions which might vary by day, patient input, symptoms and other variables)

The frequency and timing of the as needed (PRN) eye medications may be limited and controlled, such that additional extra doses out of desired windows of time and specs (for example more than one administration per 2 hour period), will not be allowed. For example, the processor 1030 may count the number of dispensing of a particular drug (e.g., the PRN drug) and, if the number of dispensings of that drug over a predetermined amount of time (e.g., 2 hours) matches or exceeds a predetermined threshold (e.g. one per 2 hours), then the processor will lock and allow the dispensing mechanism 1020 to be activated to dispense that drug until a certain amount of time has lapsed.

Various ophthalmic medications may be pre-configured into 'cartridges' 1100 that would fit in the dispenser 1000. Thus, a variety of ophthalmic medications could be contained within the dispenser 1000. In one embodiment, more than one drug type could be dispensed, for example a dispenser 1000 which contains drugs for glaucoma, infection, and lubrication. The first would be dispensed on a regular set schedule (or one altered based on the patients real-time measured data), and the as needed for eye dryness symptoms would only be dispensed via the dispenser 1000 on a PRN basis to improve eye lubrication. The PRN meds could be controlled and limited by lock-outs and dosing limits (which may be controlled by the processor 1030), similar to PCA devices for pain control used commonly which enable programming of doses, timings, lockouts, total doses within a time period.

Other utilities are possible. For example, pharmaceutical companies and contract research agencies around the world conduct lengthy and expensive clinical trials on new drugs, combinations, dosings and indications. A key component of trials is assurance that the drugs (or placebo or alternative treatment/drug arms) were actually taken. Using the dispenser 1000, the taking of the medicine, time stamped, and verified could be recorded and transmitted in a variety of ways via the dispenser 1000 to those running and analyzing any drug trial. This could include use of a camera 1220 built into the device which could take a photo of each dispensation. The dispenser 1000 can additionally include a voice recorder 1250 for the trial participant to note and record any side effects, symptoms (good and bad) or other notations. The dispenser 1000 can additionally include a touch screen 1080 for the trial participant to note and record any side effects, symptoms (good and bad) or other notations. The dispenser can record and integrate various physiologic or other measures, including but not limited to eye and related physiology data. As described in co-pending U.S. application Ser. No. 13/210,333, filed Aug. 15, 2011, the contents of which are incorporated herein by reference, the dispenser and included or remotely accessed computer could integrate various information and data relevant to the individual to inform drug dose, combination, timing and other modifications, optimizations and changes of treatment regimen. An example could include glaucoma medications. Eye pressure values could be recorded from various tonometry devices 1260 which measure intra-ocular pressure (IOP), and as trends and IOP values are determined, pre-set algorithms could inform the dispense to deliver or 'hold/skip' a dose of drugs which treat high IOP. For example a patient's IOP is running low, and the dispenser 'holds' the evening dose for one or both eyes.

In the context of a clinical trial or everyday use, a visible, and or auditory alarm, and or vibratory alarm as well transmission of reminder information via cell phone, pager, website or other modality as optional display can remind the patient or caregiver when it's time to take medication.

In a further embodiment, the contained drug products 1005a, b, c . . . may include a biocompatible identifying trackable element. By way of example, but not limitation, the dispenser 1000 also optionally can read each drug product holder 1005a, b, c . . . through the reader 1040, which may include optical or other means, if each drug container has any marker ranging from RFID or other embedded information, to use of camera or reader of many varieties to read and record a barcode, QR code, actual text, color or other attributes of each container. In this way a very detailed record of each dispensed drug could be recorded for use in compliance, clinical trials, self reporting for the patient, and could augment safety and timing of each pill/medicine dispensed. Additionally, as mentioned supra the dispenser 1000 can contain a camera which can take a picture, and optionally store and transmit a record of dispensed medications to the eye.

The dispenser 1000 may communicate to the patient by sound e.g., different beeps or alarm sounds or buzz patterns can indicate different medications and timings, or even recorded messages such as 'time to take your medication now . . . please place over your right eye and hit the 'dispense' button".

An LCD or other type of common screen or display 1080, e.g., as used in PDA's phones, digital watches, etc., can display information to the user, and also include inputs, such as ways to set the scheduling of drugs contained within.

The dispenser 1000 may be programmed directly via the screen via touch based user interface or with one or more buttons, similar to how a digital watch or timer or many other electronic devices are programmed, such as one button to control menu and an additional button(s) to set time, date windows, etc.

Voice interface, optionally including voice recognition, run by software in onboard computer, or via cell phone or via the web or other networked interface, could program the dispenser 1000 as well to set timings of alarms and other features such as to record treatment or side effects.

The dispenser 1000 may contain a small onboard battery powered computer (e.g., the processor 1030) which would also potentially be linked to data inputs and would help determine when/if dosings for the patient.

Data inputs from the user could include intra-ocular pressure, visual acuity and other visual measures, vital signs, e.g., as measured by external measurement devices 1090, which may include wearable devices 1280 on the patient that measure heart rate, blood pressure, and/or activity, and may further include optional built in accelerometer or data derived from sensors in the users mobile phone or other networked device which communicates with the dispenser 1000. Optionally an intra-ocular pressure (IOP) device 1260, or other device which can measure variables of the eyes could be integrated into the dispenser.

In accordance with the present disclosure, there are many applications for detecting patient data and utilizing this data to interact with the dispenser 1000 to alter based on prescribed algorithms and guidelines from a prescriber, e.g. an opthalmologist, etc., in which to help optimize if and when and how often a drug was to be dispensed.

Creation of 'designer' or personalized drug products 1005a, b, c . . . which contain multiple medications specific for a user (compounded medicine), and individual combination eye drug products (e.g., individually mixed drugs containing 2 or more medicines prescribed for the individual) are described in my aforesaid U.S. application Ser. No. 13/210,333, filed Aug. 15, 2011, the contents of which are incorporated herein by reference. Such drug products can also be printed with patient's name, a bar code, QR code or other identifying markings on each drug container 1005a, b, c . . . Further, such combination or compound drug products may be designed to be manufactured into containers which specifically fit the dispenser 1000. The dispenser 1000 may record their use as described, or simply contain and manually dispense.

In one embodiment, the personalized drugs or combination drugs could be 'printed' or mixed/compounded to specifications related to an individual patient, and added to a cartridge 1100 that is designed to fit within the dispenser 1000. 'Morning' and 'Evening' eye drops could be alternated such that with each dispensement the AM/PM drug(s) or combinations would be dispensed alternatively.

The dispenser 1000 may further include a button or other activation mechanism (both manual and potentially automatic or programmatic based on low levels of drug) which may be activated to order refills of contained meds. Furthermore, the processor 1030 may be configured to count or otherwise determine how full the chamber 1010 or cartridge 1100 is, and alert the user to order a refill when the chamber 1010 or cartridge 1100 is low. Alternatively, or additionally, the processor 1030 may transmit a signal to a computer located at a pharmacy or a clinician's office to automatically order a refill. The process also may include a lock-out device for preventing over use by the patient.

In another embodiment, the dispenser 1000 may include an emergency button 1280, to signal/call/alert care provider(s), ranging from doctor, EMS/911, friends and family, etc. This could alert via integrated communication via cell phone and/or the internet (Bluetooth or WiFi enabled device), and could also communicate the patient/user's position, via GPS or other marker of location.

Additionally, the dispenser 1000 may include a patient authorization element 1290, which may be any known element for authorizing a user, including for example, a fingerprint reader, voice recognition element, face recognition, retinal detection or facial recognition via an integrated camera, or keypad code.

In one embodiment, the dispenser could also issue preset or adjustable and prescribed unit volumes, e.g. as designated by the user/patient or prescriber, of medication drug or supplement in liquid or solution form. Adjusted volume/dosage could be modulated directly via inputs on the dispenser or optionally remotely, as indicated by various parameters. By way of example dosage drops could be dialed in manually, mechanically . . . i.e. 2 clicks to set 2 drops, and so forth.

Various changes may be made in the disclosure without departing from the spirit and the scope thereof. For example, other medication cartridge mechanisms for loading the dispensing device could be inserted manually by the patient, provider, pharmacist and/or, or by devices with other control mechanisms or other integrated platform to which the dispenser could be connected, i.e. to integrate possible loading mechanisms for centralized or other forms of medication containers, are possible. Also falling within the scope of the subject disclosure are methods and devices to enhance compliance and record and measure of medications by the individual. One such method is illustrated in FIG. 3. These include 'gamification', for example incentive point rewards or other similar means to help 'reward' the patient in use and compliance with their ophthalmic medications. As pictured at block 1300, a patient's use is recorded using camera 1220, displayed on the dispenser, and the image transmitted via a mobile phone to a central repository 1310 where the timing of the use is compared to a patient's programmed use for compliance. Furthermore the dispensing device could be connected by various means to any number of mobile health "Apps" which integrate compliance tracking, gamification or other means of integrating medication use for any number of conditions. Additionally, the dispenser may include a bracing mechanism, which may be fixed or adjustable, schematically shown at 1320, positioning the dispenser over the eye.

It should be emphasized that the above-described embodiments of the present portable drug dispenser are merely possible examples of implementations and are merely set forth for a clear understanding of the principles of the disclosure. Many different embodiments of the portable drug dispensers described herein may be designed and/or fabricated without departing from the spirit and scope of the disclosure. All these and other such modifications and variations are intended to be included herein within the scope of this disclosure and protected by the following claims. Therefore the scope of the disclosure is not intended to be limited except as indicated in the appended claims.

The invention claimed is:

1. A hand-held ophthalmologic dispenser comprising at least two chambers for holding different separately contained liquid ophthalmic drugs, and a dispensing mechanism configured to dispense one or more of the separately contained liquid drugs through a separate dropline associated with each of said chambers leading to and through a nozzle directly onto an eye of a patient upon activation of the dispensing mechanism, said dispenser also including at least one chamber containing a wash solution connected to each of said droplines configured to clean said droplines for further dispensing of said one or more of said liquid drugs, said dispenser further including a sensor configured to detect an open-eye condition of the patient, a trigger configured to activate the dispensing mechanism when an open-eye condition is detected, and a fixed or flexible and adjustable bracing mechanism configured for positioning the dispenser over the patient's eye.

2. The dispenser of claim 1, wherein each of said chambers has a separate dropline.

3. The dispenser of claim 1, wherein the sensor is selected from the group consisting of a camera or other optical device to detect said open-eye condition.

4. The dispenser of claim 3, further including an accelerometer or other sensor configured to detect a position of the dispenser relative to the patient; and a tonometry device.

5. The dispenser of claim 1, further including a processor configured to control and record dispensation of said liquid drugs from said chamber(s).

6. The dispenser of claim 1, wherein said chamber(s) are removable, and further including a reader for determining contents of said chambers.

7. The dispenser of claim 1, wherein the dispenser includes a device for authorizing a user to activate the dispensing mechanism.

8. The dispenser of claim 1, further comprising a lock-out device for limiting use.

9. The dispenser of claim 1, further including a processor for tracking use.

10. The dispenser of claim 1, further including a processor for tracking use and for prompting a refill.

11. The dispenser of claim 1, further including an emergency call system.

12. The dispenser of claim 1, further including a patient authorization device.

13. The dispenser of claim 1, attached to or integrated into a mobile phone case.

14. The dispenser of claim 2, wherein two or more of said droplines join at a common dropline.

15. The dispenser of claim 1, further including an integrated or removable cap to keep the nozzle area clean and sterile.

16. The dispenser of claim 1, wherein an alert indicator comprises a sound generator, a vibrator or a light.

17. The dispenser of claim 1, wherein an alert indicator comprises a programmable controller.

* * * * *